United States Patent [19]

Zviely et al.

[11] Patent Number: 5,077,440

[45] Date of Patent: Dec. 31, 1991

[54] PROCESS FOR THE PREPARATION OF 3-PHENOXYBENZYLALCOHOL

[75] Inventors: Michael Zviely; Aaron R. McMurray, both of Haifa; Joshua Hermolin, Ramat Hasharon, all of Israel

[73] Assignee: Bromine Compounds Ltd., Beer-Sheva, Israel

[21] Appl. No.: 425,417

[22] Filed: Oct. 23, 1989

[30] Foreign Application Priority Data

Oct. 24, 1988 [IL] Israel ......................................... 88135

[51] Int. Cl.$^5$ .................... C07C 29/124; C07C 33/24; C07C 41/22; C07C 43/205
[52] U.S. Cl. .............................. 568/638; 204/157.9; 568/639
[58] Field of Search ....................... 568/648, 638, 639; 204/157.9

[56] References Cited

U.S. PATENT DOCUMENTS

| | | | |
|---|---|---|---|
| 4,302,306 | 11/1981 | Katsuragawa et al. | 568/639 |
| 4,393,246 | 7/1983 | Kubo et al. | 568/639 |
| 4,694,110 | 9/1987 | Takenaka et al. | 568/638 |
| 4,709,100 | 11/1987 | Hermolin et al. | 568/639 |

FOREIGN PATENT DOCUMENTS

| | | | |
|---|---|---|---|
| 202830 | 11/1986 | European Pat. Off. | 568/638 |
| 166131 | 12/1981 | Japan | 568/638 |
| 69828 | 4/1983 | Japan | 568/638 |
| 1010525 | 1/1986 | Japan | 568/638 |
| 1072729 | 4/1986 | Japan | 568/638 |

*Primary Examiner*—J. E. Evans
*Attorney, Agent, or Firm*—Michael N. Meller

[57] ABSTRACT

In a process for the preparation of 3-phenoxybenzylalcohol, 3-phenoxytoluene is reacted with dibromodimethylhydantoin in a non-polar solvent, followed by hydrolysis of the products of the first reaction step.

The process provides highly pure 3-phenoxybenzylalcohol with high yields.

20 Claims, No Drawings

PROCESS FOR THE PREPARATION OF 3-PHENOXYBENZYLALCOHOL

BACKGROUND OF THE INVENTION

1. The Field of The Invention

The present invention relates to a process for the preparation of 3-phenoxybenzylalcohol. More particularly, the invention relates to a process by which 3-phenoxybenzylalcohol is prepared from 3-phenoxytoluene.

2. The Prior Art

3-Phenoxybenzylalcohol (mPBL) is an important intermediate in the synthesis of pyrethroid insecticides. However, because of the very high purity required for this intermediate, many of the possible preparation methods known in the art do not lead to industrially useful products.

The halogenation of 3-phenoxytoluene (mPHT) and the subsequent conversion of the resulting mixture of benzyl- and benzal-halides into mPBL or 3-phenoxybenzaldehyde (mPBA) provides a product that is contaminated as the result of the halogenation of the aromatic ring. These contaminants cannot be removed by industrially applicable and useful processes. For instance, the chlorination of the methyl group of mPHT leads to substantial amounts of ring-chlorinated contaminants.

According to German Patent Application 2402457, mPHT is chlorinated using chlorine and $PCl_3$ at temperature of 250° C., to obtain a mixture of 3-phenoxybenzylchloride (mPHT-Cl) (62.3%) and 3-phenoxybenzalchloride (mPHT-$Cl_2$) (16.3%). This mixture is refluxed with sodium acetate in acetic acid to give a mixture containing mPHT (63%), 3-phenoxybenzylacetate (14.5%) and mPBA (16.1%). On treatment with sodium borohydrate in alcoholic sodium hydroxide, this mixture gives mPBL in 80% yield (relative to the converted starting material).

According to German Patent 2707232, mPHT is chlorinated under 125W Hg lamp to obtain a mixture of (38.8%) mPHT-Cl, (53.4%) mPHT-$Cl_2$, (4.6%) 3-phenoxybenzotrichloride and (3.2%) by-products. The mixture is treated with sodium formate in formic acid to give 3-phenoxybenzylformate and mPBA. The ester is hydrolized with sodium hydroxide to give mPBL.

German Patent 2850180 teaches a process in which the product after chlorination, containing (46.9%) mPHT-Cl, (3.6%) mPHT-$Cl_2$, (46.7%) mPHT and (0.7%) ring chlorinated products, is hydrolyzed with aqueous sodium hydroxide at 180° C. to give a mixture containing (44.9%) mPBL, (4.6%) mPBA, (48.9%) mPHT, (0.2%) mPHT-Cl and (0.6%) ring chlorinated products. This mixture is mixed with aqueous sulfuric acid and toluene and oxidized with sodiumbichromate to give mPBA.

In German Patent 2850179, the chlorination products of mPHT, namely (53.4%) mPHT-Cl, (9.4%) mPHT-$Cl_2$, accompanied with (32.4%) mPHT and (4.7%) unknown components, were autoclaved with magnesium oxide and water for 3 hours at 180° C., to give (86.4%) mPBL (based on mPHT-Cl).

Japanese Patent 81166142 describes a process in which the hydrolysis was performed on a mixture containing mPHT-Cl and mPHT-$Cl_2$ by autoclaving with the carbonate or bicarbonate of sodium, potassium or calcium in water. According to this patent the reaction takes place at temperatures between 130° and 250° C., and gives a mixture of mPBL and mPBA.

In another Japanese Patent, JP 81166131, a similar chlorides mixture is hydrolized for 2 hours at 150° C. (5 atm), to give mPBL and mPBA.

Attempts to brominate mPHT with elemental bromine leads to similar problems. Therefore, brominating agents, e.g. N-bromosuccinimide and N-bromoacetamide, have been suggested, e.g., in German Patent 2810305. Recently, an improvement in the art has been reported, wherein a mixture of 3-phenoxybenzylbromide (mPHT-Br) and 3-phenoxybenzalbromide (mPHT-$Br_2$) were produced without any substantial ring bromination taking place. This process, described in GB 2175895, operates under conditions at which the mPHT is converted almost completely into mixtures of mPHT-Br/mPHT-$Br_2$, alleviating the need to recycle the starting material. However, it is necessary to further react the mixtures of mPHT-Br/mPHT-$Br_2$ in order to convert them into mPBL or mPBA, respectively.

If it is desired to prepare mPBA, this can be achieved from the abovementioned mixture in a single reaction step. Preparation of mPBL, however, can be effected only through two additional reaction steps.

It is therefore clear that it would be desirable to provide a simple process for manufacturing 3-phenoxybenzylalcohol with high purity and in high yield.

SUMMARY OF THE INVENTION

It has now been found, and this is an object of the present invention, that it is possible to provide such a process, which process provides highly pure 3-phenoxybenzylalcohol, with yields higher than 90%.

It is another object of the invention to provide such a process which can be easily carried out in a continuous manner.

DETAILED DESCRIPTION OF THE INVENTION

The process for the preparation of 3-phenoxybenzylalcohol, according to the invention, is characterized in that 3-phenoxytoluene is reacted with dibromodimethylhydantoin (DBDMH) in a non-polar solvent, followed by the hydrolysis of the product(s) of the first reaction step.

Thus, the invention consists of a two steps process for the manufacture of mPBL from mPHT, as starting material. In the first step bromination of mPHT is carried out in a non-polar solvent at temperatures which are preferably above 65° C., using dibromodimethylhydantoin, in which the molar ratio of the two reagents is in the range of 1.0:0.1 to 1.0:0.35. The optimal molar ratio is determined by the requirements for the maximum conversion of mPHT and the minimum formation of mPHT-$Br_2$. This is achieved at about 1.0:0.2 molar ratio which gives rise to about 40% conversion of mPHT and about 1.5% of mPHT-$Br_2$. The bromination is preferably carried out in non-polar solvents and in the presence of radical initiators. Such initiators, already described in GB 2175895 are selected from azo-compounds, peroxides and mixtures thereof. UV light is also a suitable initiator. Preferred initiators comprise azobisisobutyronitrile and/or benzoyl peroxide. In the second step of the process the hydrolysis of the obtained mixture (namely, mPHT, mPHT-Br [major product], and mPHT-$Br_2$ [minor product] is carried out. The hydrolysis can be carried out in two different modes: hydrolysis of the mixture mentioned above, and hydrolysis of the mixture of mPHT-Br (major product) and mPHT-Br$_2$ (minor product) after the removal of m-PHT. The hydrolysis step is done by reacting the above mixtures in presence of a basic reagent, at high temperatures and at the autogenous pressures.

Generally, these reagents are selected from hydroxides, oxides, carbonates or bicarbonates of the alkalies or the alkaline earth elements, such as sodium hydroxide, potassium hydroxide, magnesium oxide, sodium carbonate, potassium carbonate etc., in aqueous solutions. Of the above-mentioned reagents, sodium carbonate is the preferred one, because of pricing and compatibly low solution pH. It is clear, however, that many other basic reagents, such as the ones mentioned above and others, can be employed. Some of such reagents, however, will suffer from drawbacks such as relatively high price, or formation of slurry, with lower operational convenience resulting therefrom. The temperatures should be relatively high, namely over 100° C., and the pressure is above the atmospheric pressure (autogenous). The hydrolysis step can be done batchwise, but it can, also, be easily carried out in a continuous manner.

Preferred non polar solvents comprise chlorobenzene, dibromomethane, dibromoethane, dichloroethane, tetrachloroethane, tetrachloromethane and tetrachloroethylene.

The amount of non-polar solvent in the reaction mixture is also an important parameter. The preferred range is comprised between about 50% and about 90% by volume of the total reaction mixture. This is because solvent volumes higher than 90% of the total reaction mixture result in low time-space yields. On the other hand, if the solvent volume is less than 50%, ring-bromination side reactions occur to an unacceptable extent.

The bromination reaction is very aggressive. Therefore, it is preferably carried out by carefully contacting the reactants. Thus, according to a preferred embodiment of the invention, dibromodimethylhydantoin is gradually added to the reaction mixture. Alternatively, DBDMH and mPHT can be added separately and continuously into the reaction mixture.

According to a preferred embodiment of the invention, about 10% of the radical initiator is added to the reactor at the beginning of the reaction, in order to assure controlled start. If the total amount of initiator is added at the beginning, insufficient free radicals may be generated throughout the reaction. In addition, a large volume of nitrogen would be released in the reactor, causing serious operation problems. Of course, when the initiator is UV or visible light, the said addition refers to the exposure of the reactants to irradiation.

As will be apparent to the skilled chemist, the bromination reaction can be carried out either in a semi-continuous or in a continuous manner, with the required changes.

While, as stated, it will usually be convenient to separate DMH and the solvent before passing to the hydrolysis step, direct hydrolysis of mPHT-Br, in the presence or not of residual mPHT, can be carried out, provided that DMH is previously removed from the reaction mixture.

The above and other characteristics and advantages of the invention will be further illustrated by the following non-limitative examples.

EXAMPLE 1

A slurry containing 186.1 g (0.65 mole) of 1.3-dibromodimethylhydantoin (DBDMH) (IMI), 7.04 g (0.043 mole) of azo-isobutyronitrile (Merck), and 380 cc of tetrachloroethylene, was introduced into a three-necked reactor containing a stirred and boiling solution containing 399 g (2.17 mole) of 3-phenoxytoluene (Fluka, mPHT/DBDMH molar ratio of 1.0:0.3) in 380 cc of tetrachloroethylene.

After the addition of slurry was completed, the reaction mixture was cooled and the dimethylhydantoin (DMH) was filtered off, washed with two portions of tetrachloroethylene (each of 50 ml).

The solvent was evaporated in vacuo (20 mm Hg) and the reaction mixture was analyzed by 1H-NMR (200 MHz BRUKER), using 1,1,2,2-tetrachloroethane as internal standard.

The following results were obtained:

| | |
|---|---|
| 3-phenoxytoluene | 39.7% |
| 3-phenoxybenzylbromide | 54.0% |
| 3-phenoxybenzalbromide | 5.1% |
| 6-bromo-3-phenoxytoluene | n.d.* (<0.1%) |
| 6-bromo-3-phenoxybenzylbromide | n.d. (<0.1%) |

*n.d. = non detectable

EXAMPLE 2

The above procedure was repeated with the following quantities of reagents:
385.5 g (2.068 mole) of 3-phenoxytoluene
118.3 g (0.44 mole) of 1,3-dibromodimethylhydantoin
2.91 g (0.018 mole) of azo-isobutyronitrile
725 cc of tetrachloroethylene
mPHT/DBDMH molar ratio of 1.0:0.2

The results were as follows:

| | |
|---|---|
| 3-phenoxytoluene | 56.2% |
| 3-phenoxybenzylbromide | 40.6% |
| 3-phenoxybenzalbromide | 1.2% |
| 6-bromo-3-phenoxytoluene | n.d. (<0.1%) |
| 6-bromo-3-phenoxybenzylbromide | n.d. (<0.1%) |

EXAMPLE 3

The above procedure was repeated with the following quantities of reagents:
399.4 g (2.17 mole) of 3-phenoxytoluene
74.5 g (0.278 mole) of 1.3-dibromodimethylhydantoin
2.82 g (0.017 mole) of azo-isobutyronitrile
700 cc of tetrachloroethylene
mPHT/DBDMH molar ratio of 1.0:0.13

The results were as follows:

| | |
|---|---|
| 3-phenoxytoluene | 70.0% |
| 3-phenoxybenzylbromide | 26.1% |
| 3-phenoxybenzalbromide | 0.4% |
| 6-bromo-3-phenoxytoluene | n.d. (<0.1%) |
| 6-bromo-3-phenoxybenzylbromide | n.d. (<0.1%) |

EXAMPLE 4

Example 2 was repeated, but using chlorobenzene instead of tetrachloroethylene. Comparable results were obtained.

EXAMPLE 5

Example 2 was repeated, using dibromomethane instead of tetrachloroethylene. The result obtained as in Example 2.

EXAMPLE 6

A 1 liter reaction vessel containing 150 ml of tetrachloroethylene was preheated to reflux temperature. To this reactor there were added, through two separate pumps, the following ingredients:
385.5 g (2.06 moles) of 3-phenoxytoluene in 200 ml of tetrachloroethylene; and
118.3 g (0.44 moles) of 1,3-dibromodimethylhydantoin, together with 2.91 g (0.018 moles) of azo-isobutyronitrile in 365 ml of tetrachloroethylene.

The mean residence time in the reactor was about 10 minutes, and the mPHT/DBDMH molar ratio was 1.0:0.2. The results of this continuous bromination were comparable to those obtained in Example 2.

EXAMPLE 7

The mixture obtained in example 1 was distilled to remove 3-phenoxytoluene, using 5 theoretical plates column. A fraction collected at 83° C. (1 mm Hg) contained the following:

| | |
|---|---|
| 3-phenoxytoluene | 97.5% |
| 3-phenoxybenzylbromide | 0.3% |

The composition of the bottom fraction was as follows:

| | |
|---|---|
| 3-phenoxytoluene | n.d. (<0.1%) |
| 3-phenoxybenzylbromide | 92.6% |
| 3-phenoxybenzalbromide | 7.3% |

EXAMPLE 8

A sample of the product obtained in example 3, containing 52.5 g 3-phenoxytoluene (0.285 moles), 19.57 g 3-phenoxybenzylbromide (0.074 moles) and 0.322 g 3-phenoxybenzalbromide (0.001 moles) was introduced into a stainless steel autoclave with 165 g 9% sodium carbonate aqueous solution (0.14 moles). The mixture was heated to 150° C. and a pressure of 5 atm. developed. The reaction mixture was kept at these conditions for 2 hours. After cooling, two phases separated.

The aqueous upper phase was extracted with tetrachloroethylene and the organic solutions were unified. The solvent was evaporated and the crude mixture was analyzed by 1H-NMR using 1,1,2,2-tetrachloroethane as internal standard.

The results were as follows:

| | |
|---|---|
| 3-phenoxytoluene | 76.6% |
| 3-phenoxybenzyl alcohol | 20.0% |
| 3-phenoxybenzaldehyde | n.d. (<0.1%) |
| 3-phenoxybenzylbromide | n.d. (<0.1%) |
| 3-phenoxybenzalbromide | n.d. (<0.1%) |
| 6-bromo-3-phenoxybenzyl alcohol | n.d. (<0.1%) |
| 3-phenoxybenzylether | 3.3% |

These results represent a yield of ca. 91% of 3-phenoxybenzyl alcohol (relative to the 3-phenoxybenzylbromide introduced).

EXAMPLE 9

The following reagents were continuously fed into a 0.5 lit. pressure vessel, using two pumps, at 180° C. and at a pressure of about 8 bars:
432 g (2.36 moles) 3-phenoxytoluene, 296.8 g (1.12 moles) 3-phenoxybenzylbromide and 4.88 g (0.014 moles) of 3-phenoxybenzalbromide in 2,268 g of tetrachloroethylene; and
227.2 g (2.12 moles) of sodium carbonate in 4,600 ml of water.

The mean residence time in the reaction vessel was 90 minutes. The continuous hydrolysis gave results similar to those obtained in the batch mode of Example 8.

We claim:

1. A process for the preparation of 3-phenoxybenzylalcohol, which comprises reacting 3-phenoxytoluene with dibromodimethylhydantoin in a non-polar solvent, followed by hydrolysis of the products of the first reaction step wherein the molar ratio of 3-phenoxytoluene to dibromodimethylhydantoin in the range of 1.0:0.1 to 1.0:0.35.

2. A process according to claim 1, wherein the non-polar solvent is selected from the group consisting of chlorobenzene, dibromomethane, dichloroethane, tetrachloroethane, and tetrachloromethane.

3. A process according to claim 2, wherein the non-polar solvent is tetrachloroethane.

4. A process according to claim 1 wherein the bromination reaction is carried out at a temperature comprised between 65° C. and the boiling point of the reaction mixture.

5. A process according to claim 1, wherein the amount of nonpolar solvent is between 50% and 90% by volume of the reactants.

6. A process according to claim 1, wherein 3-phenoxytoluene and dibromodimethylhydantoin are gradually added to the reaction mixture.

7. A process according to claim 6, wherein the bromination reaction is carried out in the presence of a radical initiator selected from a compound containing azo-groups, peroxides and mixtures thereof, ultraviolet or visible light and a combination of two or more of said initiators.

8. A process according to claim 7, wherein the radical initiator is azo-bis-isobutyronitrile, benzoylperoxide or mixture thereof.

9. A process according to claim 7, wherein about 10% of the radical initiator is added to the reactor at the beginning of the reaction.

10. A process according to claim 1, wherein the bromination reaction is carried out in a semi-continuous or continuous manner.

11. A process according to claim 1, wherein 3-phenoxybenzylbromide is hydrolyzed, after removal of the dimethylhydantoin, in the presence of tetrachloroethylene, residual 3-phenoxytoluene or mixtures thereof.

12. A process according to claim 1, wherein, prior to the hydrolysis step, the unreacted dimethylhydantoin is filtered-off.

13. A process according to claim 12, wherein unreacted 3-phenoxytoluene and the solvent are removed by distillation prior to to the hydrolysis step.

14. A process according to claim 1, wherein the hydrolysis is carried out at a temperature of at least 100° C., and at autogenous pressure.

15. A process according to claim 14, wherein the temperature is between 130° and 250° C.

16. A process according to claim 14, wherein the hydrolysis is carried out in aqueous solutions or slurries of metal oxides, hydroxides or carbonates.

17. A process according to claim 16, wherein the metal ion is selected from among Na, K, Ca, or Mg, or mixtures thereof.

18. A process according to claim 11, wherein the hydrolysis of the mixture of 3-phenoxybenzylbromide, solvent and residual 3-phenoxytoluene is carried out batchwise or in a continuous manner.

19. A process according to claim 1 wherein the nonpolar solvent is tetrachloroethylene.

20. A process according to claim 1 wherein the molar ratio of 3-phenoxytoluene to dibromodimethylhydantoin is 1.0:0.2.

* * * * *